US009707228B2

(12) United States Patent
Heng et al.

(10) Patent No.: US 9,707,228 B2
(45) Date of Patent: Jul. 18, 2017

(54) DRY POWDER FORMULATION

(71) Applicants: Agency for Science, Technology and Research, Singapore (SG); National University Hospital, Singapore (SG)

(72) Inventors: Desmond Heng, Jurong Island (SG); Sie Huey Lee, Jurong Island (SG); Jeanette Teo, Singapore (SG); Wai Kiong Ng, Jurong Island (SG); Reginald Tan, Jurong Island (SG)

(73) Assignees: Agency for Science, Technology and Research, Singapore (SG); National University Hospital, Singapore (SG)

( * ) Notice: Subject to any disclaimer, the term of this patent is extended or adjusted under 35 U.S.C. 154(b) by 0 days.

(21) Appl. No.: 14/402,060

(22) PCT Filed: May 21, 2013

(86) PCT No.: PCT/SG2013/000207
§ 371 (c)(1),
(2) Date: Nov. 18, 2014

(87) PCT Pub. No.: WO2013/176622
PCT Pub. Date: Nov. 28, 2013

(65) Prior Publication Data
US 2015/0132386 A1 May 14, 2015

(30) Foreign Application Priority Data

May 21, 2012 (SG) .............................. 201203712-3

(51) Int. Cl.
| *A61K 31/496* | (2006.01) |
| *A61K 9/00* | (2006.01) |
| *A61K 31/4375* | (2006.01) |
| *A61K 45/06* | (2006.01) |
| *A61K 31/4709* | (2006.01) |
| *A61K 31/4745* | (2006.01) |
| *A61K 31/5383* | (2006.01) |
| *A61K 31/542* | (2006.01) |

(52) U.S. Cl.
CPC .......... *A61K 31/496* (2013.01); *A61K 9/0075* (2013.01); *A61K 31/4375* (2013.01); *A61K 31/4709* (2013.01); *A61K 31/4745* (2013.01); *A61K 31/5383* (2013.01); *A61K 31/542* (2013.01); *A61K 45/06* (2013.01)

(58) Field of Classification Search
CPC .. A61K 45/06; A61K 9/0075; A61K 31/4375; A61K 31/4745; A61K 31/542
See application file for complete search history.

(56) References Cited

U.S. PATENT DOCUMENTS

| 2003/0186894 | A1* | 10/2003 | Kuo | ..................... A61K 9/0075 |
| | | | | 514/21.91 |
| 2006/0280691 | A1* | 12/2006 | Wang | .................. A61K 9/0075 |
| | | | | 424/46 |
| 2007/0065373 | A1* | 3/2007 | Morton | ................ A61K 9/0073 |
| | | | | 424/46 |
| 2011/0150983 | A1* | 6/2011 | Cipolla | ................ A61K 9/0043 |
| | | | | 424/450 |

FOREIGN PATENT DOCUMENTS

| WO | WO-2006/125132 | 11/2006 |
| WO | WO-2009/044141 | 4/2009 |
| WO | WO-2010/111641 | 9/2010 |
| WO | WO-2011/050206 | 4/2011 |
| WO | WO-2013/176622 | 11/2013 |

OTHER PUBLICATIONS

"International Application No. PCT/SG2013/000207, International Preliminary Report on Patentability mailed Sep. 5, 2014", (Sep. 5, 2014), 21 pgs.
"International Application No. PCT/SG2013/000207, International Search Report mailed Jul. 1, 2013", (Jul. 1, 2013), 7 pgs.
Adi, Handoko, et al., "Controlled release antibiotics for dry powder lung delivery", Drug Development and Industrial Pharmacy, Jan. 2010, vol. 36, No. 1 : pp. 119-126, (Jan. 2010), 119-126.
Pankey, George A., et al., "In Vitro Synergy of Ciprofloxacin and Gatifloxacin against Ciprofloxacin-Resistant Pseudomonas aeruginosa", Antimicrobial Agents and Chemotherapy, vol. 49, No. 7, Jul. 2005, p. 2959-2964, (Jul. 2005), 2959-2964.

* cited by examiner

*Primary Examiner* — Mina Haghighatian
(74) *Attorney, Agent, or Firm* — Schwegman Lundberg & Woessner, P.A.

(57) ABSTRACT

A dry powder formulation comprising a combination of at least a first pharmaceutically active quinolone and a second pharmaceutically active quinolone.

20 Claims, 2 Drawing Sheets

DRY POWDER FORMULATION

PRIORITY CLAIM TO RELATED APPLICATIONS

This application is a U.S. national stage application filed under 35 U.S.C. §371 from International Application Serial No. PCT/SG2013/000207, which was filed May 21, 2013, and published as WO 2013/176622 on Nov. 28, 2013, and which claims priority to Singapore Application No. 201203712-3, filed May 21, 2012, which applications and publication are incorporated by reference as if reproduced herein and made a part hereof in their entirety, and the benefit of priority of each of which is claimed herein.

TECHNICAL FIELD

The present invention generally relates to a dry powder formulation. The present invention also relates to a method of preparing the dry powder formulation.

BACKGROUND

Pharmaceutical compositions may be administered by inhalation to or through the lung of a patient.

Typical pharmaceutical compositions combine pharmacologic activity with pharmaceutical properties, and may be delivered by means of a delivery device (such as a dry powder inhaler) to the targeted pulmonary system of a subject of treatment.

A combination of intrinsic physicochemical properties and other particle characteristics (e.g. shape and surface area) affects the interactive forces and aerodynamic properties of these particles within such formulations. These important properties in turn affect fluidization, dispersion, delivery, and ultimately deposition in the peripheral airways and lungs.

Commonly, in dry powder formulations, a dose of the pharmaceutical composition is positioned within an aerosolization chamber, where it is to be aerosolized. Such compositions are therefore required to be easily and highly aerosolizable in order to clear the composition from the inhaler device. Subsequently, the aerosolized particles are dispersed into a respirable form by means of an airflow provided by a pressurized source of gas, or by the patient's own respiratory effort. Estimates of aerosolizibility and dispersibility may be made by measuring the emitted dose and fine particle fraction of the composition, respectively.

To enable aerosolized particles to settle in the targeted regions of the lung associated with local and/or systemic drug delivery, the particle size must be carefully considered. In general, one of the main factors which determines the average particle size of a powdered composition is the selection of a suitable process from existing powder technologies. In addition, if the cohesive forces (which are dependent on the size of particles) acting on the powder are pronounced, the designed shear of a provided airflow may not be sufficient to separate an included drug from the carrier particles, and will subsequently result in low deposition efficiencies within the targeted areas of the pulmonary system.

In general, particles which are of an aerodynamic diameter greater than 5 μm generally tend to be deposited within the mouth or throat, and therefore offer little therapeutic benefit to a patient. In contrast, particles having an aerodynamic diameter smaller than 0.5 μm generally do not settle out of a provided air flow to stay deposited in the lungs, and may undesirably be exhaled by a patient administered such a formulation.

There is therefore a need to provide formulations which are better designed for inhalation that overcome, or at least ameliorate, one or more of the disadvantages of existing inhaled-formulations as described above.

SUMMARY

According to a first aspect, there is provided a dry powder formulation comprising a combination of at least a first pharmaceutically active quinolone and a second pharmaceutically active quinolone.

Advantageously, the combination of the first and second pharmaceutically active quinolones may be a synergistic combination. Hence, the dry powder formulation may be more effective against an infection as compared to just the mere sum of the anti-infective effects of the two quinolones when used separately. Having a synergistic combination of the two quinolones may broaden the antimicrobial spectrum and may aid in preventing the emergence/re-emergence of resistant microbes such as bacteria. The synergistic combination of the two quinolones may lower the dose of the individual quinolones, leading to, a reduction in the side effects and the treatment costs.

The dry powder formulation may be administered via a dry power inhaler. The dry powder formulation may not require administration via a nebulizer and hence may not be present in an aerosol form from a solution or suspension. Due to the use of an inhaler as compared to a nebulizer, a higher fine particle fraction of the powdered quinolones may be administered as compared to that achievable by a nebulizer (which is about 10% or less). In addition, the dry powder inhaler can be used to administer the drug combination without any substantial clogging of the inhaler, unlike when using a nebulizer to co-nebulize two drugs as there is a risk that the quinolones may precipitate in solution and clog the nebulizer. Further, the dry powder formulation may be more stable as compared to a quinolone solution or suspension since the quinolones are present as powdered particles. Due to the greater stability of the dry powder formulation, the formulation can be stored for a longer period of time.

The dry powder formulation may be a combination of only the first and second pharmaceutically active quinolones and may not require the addition of a third fluoroquinolone. However, the dry powder formulation may contain additional active ingredients that are not quinolones and which may have a beneficial medical effect on a patient. The additional active ingredient may be a mucolytic and/or anti-inflammatory agent(s).

According to a second aspect, there is provided a method for preparing a dry powder formulation comprising the step of forming particles of at least a first pharmaceutically active quinolone and a second pharmaceutically active quinolone.

According to a third aspect, there is provided a dry powder inhaler comprising a dry powder formulation having a combination of at least a first pharmaceutically active quinolone and a second pharmaceutically active quinolone.

The dry powder inhaler may be portable and easy to use. Hence, the use of the dry powder inhaler to administer the dry powder formulation may enhance patient compliance.

According to a fourth aspect, there is provided a dry powder formulation as defined above for use in therapy.

According to a fifth aspect, there is provided a dry powder formulation as defined above for use in treating a bacterial infection in a patient.

According to a sixth aspect, there is provided use of the dry powder formulation as defined above in the manufacture of a medicament for the treatment of a bacterial infection in a patient.

DEFINITIONS

The following words and terms used herein shall have the meaning indicated:

The term "dry powder formulation" refers to a formulation that contains finely dispersed solid particles having a certain particle size distribution that are capable of (i) being readily dispersed in or by means of an inhaler and (ii) be administered to a subject via inhalation so that a portion of the particles reach the lungs. Due to the size of the particles which is defined by their aerodynamic diameters, these particles can be suitable for pulmonary administration. A dry powder formulation typically contains less than about 15% moisture, less than 11% moisture, less than about 8% moisture, less than 5% moisture, less than 3% moisture or less than 1% moisture. The particles may be in micron-sized or nano-sized. The particles may have a narrow particle size distribution.

The term "micro-sized" is to be interpreted broadly to refer to an average particle size of between about 1 μm to about 10 μm. The particle size may refer to the diameter of the particles where they are substantially spherical. The particles may be non-spherical and the particle size range may refer to the equivalent diameter of the particles relative to spherical particles.

The term "nano-sized" is to be interpreted broadly to refer to an average particle size of less than about 1000 nm, particularly between about 50 nm to about 1000 nm, more particularly less than about 500 nm. The particle size may refer to the diameter of the particles where they are substantially spherical. The particles may be non-spherical and the particle size range may refer to the equivalent diameter of the particles relative to spherical particles.

The "narrow particle size distribution" is to be interpreted broadly to refer to a span value of the solid particles as being less than about 2. The span value is defined as Span= ([particle diameter at 90% cumulative size]−[particle diameter at 10% cumulative size])/[particle diameter at 50% cumulative size], or defined arithmetically as $(D_{90}-D_{10})/D_{50}$.

The term "combination" is to be interpreted broadly to refer to a mixture of two discrete pharmaceutically active quinolones.

The term "synergistic combination" is to be interpreted broadly to refer to a mixture of two discrete pharmaceutically active quinolones that have a greater antimicrobial activity than the sum of the antimicrobial activity of the pharmaceutically active quinolones taken individually.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a dry powder formulation will now be disclosed. The dry powder formulation comprises a combination of at least a first pharmaceutically active quinolone and a second pharmaceutically active quinolone.

In the dry powder formulation, the ratio of the first pharmaceutically active quinolone and the second pharmaceutically active quinolone may be selected in a range that provides a synergistic effect on a microbial infection.

The ratio of the first pharmaceutically active quinolone to the second pharmaceutically active quinolone may be at least 1:2 (such as from 1:2 to 1:100, 1:3, 1:2.5, 1:10 or 1:100). By having the quinolones in this ratio, this ensures that not only do the quinolones exert an antimicrobial effect, but that the antimicrobial effect is a synergistic one. Hence, the quinolones in this ratio may work in a synergistic manner to prevent, treat or at least alleviate some of the symptoms associated with a microbial infection, such as a bacterial infection.

This ratio may be obtained by determining the minimum inhibitory concentration (MIC) of each individual quinolone against a target microorganism. By knowing the MIC of each individual quinolone, the ratio of the MICs can be used as a guideline to arrive at the final workable proportion. The MIC values are important as they provide preliminary guidance on the required therapeutic dose of each quinolone in the combination powder formulation.

The first and second quinolones may independently be selected from fluoroquinolones. The fluoroquinolone may be selected from the group consisting of ciprofloxacin, gatifloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gemifloxacin, moxifloxacin, sitafloxacin, trovafloxacin, prulifloxacin and pharmaceutically acceptable salts thereof. In one embodiment, the first pharmaceutically active quinolone is ciprofloxacin (1-cyclopropyl-6-fluoro-4-oxo-7-(piperazin-1-yl)-quinoline-3-carboxylic acid) and the second pharmaceutically active quinolone is gatifloxacin (-cyclopropyl-6-fluoro-8-methoxy-7-(3-methylpiperazin-1-yl)-4-oxo-quinoline-3-carboxylic acid), or more specifically, the first pharmaceutically active quinolone is ciprofloxacin hydrochloride and the second pharmaceutically active quinolone is gatifloxacin hydrochloride. Hence, the ratio of the ciprofloxacin hydrochloride to the gatifloxacin hydrochloride may be at least 1:2. In one embodiment, the ratio of the ciprofloxacin hydrochloride to the gatifloxacin hydrochloride may be about 1:2.5. By having the ciprofloxacin hydrochloride and the gatifloxacin hydrochloride in this ratio, these drugs work in a synergistic manner against a bacterial infection.

The first and second quinolones may be present in the formulation in powder form. The powder may be comprised of nanoparticles or microparticles. The particles may be respirable-sized particles that may be administered via the pulmonary route.

The first and second quinolones may be present in the formulation in the form of particles having a narrow particle size distribution.

The particles may have a particle size in the range of about 500 nm to about 4 µm, about 800 nm to about 3 µm, about 900 nm to about 2 µm, about 1 µm to about 5 µm, about 1 µm to about 3 µm, about 1 µm to about 2 µm or about 1 µm to about 1.1 µm.

The particles may have a mono-modal size distribution with a span $(D_{90}-D_{10})/D_{50}$ of about 0.5 to about 2, about 1 to about 2 or about 1 to about 1.5. In one embodiment, the span may be about 1 or may be less than 1.

The first quinolone may have the same particle size as the second quinolone or the first quinolone may have a different particle size as compared to the second quinolone.

The particles may have a fine particle fraction in the range of about 1% to about 99%, about 10% to about 90%, about 20% to about 80%, about 30% to about 70%, about 40% to about 60%, about 40% to about 50% or about 40% to about 55%. The particles may have a fine particle fraction of about 40%. The particles may have a fine particle fraction of about 50%.

The dry powder formulation of the present invention can comprise further components which are commonly used in the preparation of a dry powder formulation that is to be administered using a dry powder inhaler. Thus, the dry powder formulation may further comprise at least one excipient. In general, excipients are used to enhance the physical or chemical stability of the active pharmaceutical ingredient, its mechanical properties, and/or its pharmaceutical properties, such as dissolution and permeation. In dry powder formulations, excipients function as carrier particles. Usually, no more than a few milligrams of drug need to be delivered, and excipients provide bulk, which improves handling, dispensing, and metering of the drug. Excipients also reduce drug cohesiveness by occupying the high-energy sites of the drug particles. An example of such an excipient comprises a sugar, such as lactose or mannitol or glucose. Other excipients can be phospholipids, such as phosphatidylcholine and cholesterol. Excipients can make up over 99% of the dry powder inhaler formulation by weight. Despite the apparent lack of choices, the excipient must be carefully selected; physicochemical properties such as size and morphology profoundly affect the performance of the formulation. The adhesive forces must be carefully considered; inadequate separation of drug and carrier is the main reason for deposition problems. The dry powder inhaler formulator may also choose to modify the excipient before combining it with the antibiotics. It should also be noted that excipients are not always required.

The dry powder inhaler formulation may further comprise a mucolytic agent or an anti-inflammatory agent. A mucolytic agent can include, but is not limited to any one of the following, a lysozyme, ambroxol hydrochloride, sodium chloride, N-acetylcysteine, or mannitol. An anti-inflammatory agent can include, but is not limited to any one of the following, a steroid or a non-steroidal anti-inflammatory drug (such as aspirin, ibuprofen, naproxen). It is also possible to use more than one mucolytic agent or anti-inflammatory agent in the dry powder inhaler formulation of the present invention.

The dry powder inhaler formulation may further comprise a sugar or sugar alcohol. A sugar or sugar alcohol can be, but is not limited to any one of the following, trehalose, sorbitol, raffinose or dextrose. It is also possible to use more than one sugar or sugar alcohol in the dry powder inhaler formulation of the present invention.

The dry powder inhaler formulation may further comprise a lubricant. A lubricant can be, but is not limited to any one of the following, leucine, magnesium stearate, sodium stearate or polyethylene glycol. It is also possible to use more than one lubricant in the dry powder inhaler formulation of the present invention.

The dry powder inhaler formulation may further comprise a polymer coating. A polymer coating can include, but is not limited to any one of the following, chitosan, polyvinyl alcohol, polylactic-co-glycolic acid, or sugar polymers (e.g. dextran, dextrin). It is also possible to use more than one kind of polymer coating in the dry powder inhaler formulation of the present invention.

In addition to the two quinolones described herein, the dry powder formulation may also comprise further pharmaceutically active ingredients which are not quinolones. For example, the formulation may comprise a pharmaceutical composition used for treating lung cancer, steroids (e.g. budesonide), beta-2-agonists (e.g. salbutamol sulphate), anticholinergics (e.g. ipratropium bromide), mucolytic agents (e.g. lysozyme, ambroxol hydrochloride), substances added to improve wound healing (e.g. heparin), anti-histimine (allergy, cough) (e.g. cetrizine hydrochloride) or decongestants (e.g. pseudoephedrine).

The dry powder formulation may be formulated for administration via a dry powder inhaler, including a metered dose inhaler.

It is to be noted that the dry powder formulation is not one that is administered via a nebulizer and is hence different from a solution formulation.

There is also provided a method for preparing a dry powder formulation comprising the step of forming particles of at least a first pharmaceutically active quinolone and a second pharmaceutically active quinolone.

The step of forming the particles may comprise the step of co-spray drying a binary system of aqueous solutions of the first pharmaceutically active quinolone and the second pharmaceutically active quinolone. The aqueous solutions may be provided at a weight ratio in the range of 1:2 to 1:100 or 1:2 to 1:8. In an embodiment where a formulation of ciprofloxacin hydrochloride and gatifloxacin hydrochloride is prepared, the aqueous solutions are aqueous solutions of ciprofloxacin hydrochloride and gatifloxacin hydrochloride that are provided at a weight ratio of about 1:2.5, about 0.5:4, about 1:4, about 1.5:4, about 0.5:3, about 0.5:3.5, about 1:2 or about 1:2.5. Due to the step of spray drying, the first pharmaceutically active quinolone and the second pharmaceutically active quinolone may be combined in the same spray-dried particle.

Alternatively or additionally, the step of forming the particles may comprise forming co-crystals via co-grinding or co-precipitation, co-freeze drying or co-spray freeze drying.

The co-spray drying may be undertaken in a suitable spray dryer. For example, a spray dryer using rotary atomization such as the Mobile Minor™ spray drier by Niro A/S of Søborg, Denmark, a spray dryer using nozzle atomizers such as the Büchi™ 290 laboratory scale spray dryer or a spray drying based on ultrasonic atomization such as the Buchi™ B-90 Nano Spray Dryer from BÜCHI Labortechnik AG of Flawil, Switzerland can be used.

Generally, during spray-drying, heat from a hot gas such as heated air or nitrogen is used to evaporate the solutions in which the quinolones are present in. The aqueous solutions are atomized by an atomizer in the spray dryer to form an atomized droplet wherein the liquid of the atomized droplet is rapidly evaporated by application of heat. Due to the small nature of the atomized droplet, and the application of heat, the liquid medium is rapidly evaporated, leaving dry particles of the quinolones.

The physical properties of the spray-dried quinolone particles depend on a number of parameters such as direction of flow of the drying gas in the drying chamber; the degree and uniformity of atomization due to the type of atomizer used; the temperature of the aqueous solutions and efficiency of the collection mechanism.

The flow of the drying gas in the drying chamber may be substantially opposite to the flow of the atomized solution (that is, countercurrent flow) or the flow of the drying gas in the drying chamber may be in the same direction as the flow of the atomized solution (that is, cocurrent flow). Some spray dryers may combine both countercurrent and cocurrent flow in the drying chamber. The type of flow pattern in the drying chamber may aid in the generation of turbulence in the drying chamber and hence, may lead to an increased rate of interaction between the drying gas and the atomized droplets in order to increase the rate of heat transfer from the drying gas to the atomized droplets.

The inlet temperature of the drying gas into the spray dryer may be in a range selected from the group consisting of about 50° C. to about 150° C.; about 50° C. to about 70° C.; about 50° C. to about 90° C.; about 50° C. to about 110° C.; about 50° C. to about 130° C.; about 70° C. to about 150° C.; about 90° C. to about 150° C.; about 110° C. to about 150° C. and about 130° C. to about 150° C. The outlet temperature may be dependent on the inlet temperature selected and is typically in the range of about 20° C. to about 90° C. In one embodiment, the outlet temperature may be kept below 50° C. in order to ensure that the biological activity of the quinolone is retained.

The nozzle size of the spray dryer may be 4 µm, 5.5 µm or 7 µm.

The evaporating capacity of the spray dryer may be about 0.2 l/h $H_2O$ or less.

The concentration of the first and/or second quinolone may be selected from about 1 mg/ml to about 10 mg/ml. The flow-rate of the first and/or second quinolone may be selected from about 1 mL/h to about 25 mL/h.

There is also provided a dry powder inhaler comprising a dry powder formulation having a combination of at least a first pharmaceutically active quinolone and a second pharmaceutically active quinolone. The dry powder inhaler may include a metered dose inhaler. The dry powder inhaler may be portable and easy to use. The dry powder inhaler may be a non-portable inhalator. The dry powder inhaler may be designed for single use or multiple use or in other words as a re-usable or disposable inhaler.

The dry powder inhaler may disperse the dry powder formulation at a rate between about 30 to about 100 L/min, 30 to about 80 L/min, 30 to about 70 L/min, 40 to about 90 L/min, 30 to about 60 L/min, 40 to about 70 L/min, 50 to about 70 L/min, 30 L/min, 40 L/min, 50 L/min, 60 L/min or 70 L/min. Administration at these rates can achieve a substantially uniform deposition profile across all impaction stages.

The dry powder formulation may be for use in therapy. The dry powder formulation may be for use in treating a bacterial infection in a patient. The bacterial infection may be a pulmonary infection. The bacterial infection may be caused by a bacteria selected from the group consisting of Gram-negative bacilli such as the genera of *Pseudomonas*, *Escherichia*, *Haemophilus*, *Klebsiella*, *Legionella*, *Moraxella*, *Proteus*, *Acinetobacter*, or Gram-positive bacilli of the genera *Staphylococcus*, *Streptococcus*, *Enterococcus*, *Mycobacterium*, *Corynebacterium* and *Mycoplasma*.

The bacterial infection may be caused by a bacteria selected from the group consisting of *Escherichia coli*, *Haemophilus influenzae*, *Klebsiella pneumoniae*, *Legionella pneumophila*, *Moraxella catarrhalis*, *Proteus mirabilis*, *Pseudomonas aeruginosa*, *Acinetobacter baumannii*, *Staphylococcus aureus*, *Streptococcus pneumoniae*, *Staphylococcus epidermis*, *Enterococcus faecalis*, *Streptococcus pyogenes*, *Mycobacterium tuberculosis*, non-tuberculous mycobacteria, *Corynebacterium diphtheria* and *Mycoplasma pneumoniae*.

The patient may be an animal, such as a human. The patient may be one suffering from cystic fibrosis. The bacteria may be of the genus *Pseudomonas* which is pathogenic to the patient. The bacteria may be *Pseudomonas aeruginosa*.

There is also provided the use of the dry powder formulation in the manufacture of a medicament for the treatment of a bacterial infection in a patient.

Pulmonary infection may be due to bacterial infections. Upper respiratory tract infections may include pharyngitis, eiglottitis, laryngitis tracheitis and lower respiratory tract infections may include bronchitis, bronchiolitis and pneumonia. The bacterial pulmonary infection may also result from tuberculosis. Patients suffering from chronic obstructive pulmonary disease (COPD), cystic fibrosis and asthma may also be prone to pulmonary infections.

The medicament may be administered via the pulmonary route into the respiratory tract.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figure 1:
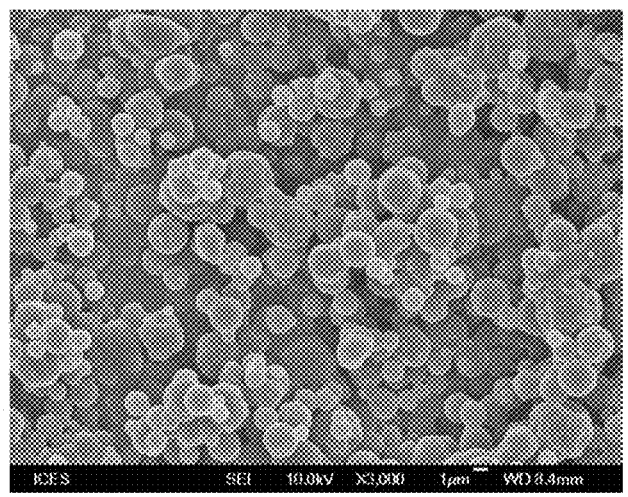
FIG. 1 is a scanning electron microscopy image at 3,000 times magnification of the spray-dried particles of ciprofloxacin hydrochloride and gatifloxacin hydrochloride (SD-CIP/GAT).

Non-limiting examples of the invention will be further described in greater detail by reference to specific Examples, which should not be construed as in any way limiting the scope of the invention.

Example 1

A dry powder formulation made up of a binary combination powder (SD-CIP/GAT) of ciprofloxacin hydrochloride (CIP) and gatifloxacin hydrochloride (GAT) was obtained by co-spray drying an aqueous solution of the above drugs using a Buchi Nano Spray Dryer B-90 (from BUCHI Labortechnik AG of Flawil, Switzerland) with operating parameters as detailed in Table 1.

Ciprofloxacin hydrochloride and gatifloxacin hydrochloride were supplied by Junda Pharmaceutical Co. Ltd (of Guangzhou of China). The aqueous solution of ciprofloxacin hydrochloride and gatifloxacin hydrochloride (at a weight ratio of 1:2.5) was obtained by dissolving both drugs together in water. The weight ratio of the individual quinolone in the solution (as well as in the resultant spray-dried particle) was based on the quinolone's minimum inhibitory concentration (MIC). The MIC was experimentally determined and a ratio of the quinolones was obtained as a guideline in developing the final workable proportion. The quinolones' MIC values were important as they provided preliminary guidance on the required therapeutic dose of each quinolone in the binary (SD-CIP/GAT) powder formulation (i.e. combination ratios). The MICs of the various quinolones for the bacteria *Pseudomonas aeruginosa* different bacteria were determined via the microdilution method and used to determine the desired binary drug proportions. For the bacteria *Pseudomonas aeruginosa*, since $MIC_{CIP}$:$MIC_{GAT}$ is 1:2 (actual values are 0.25 μg/ml:0.5 μg/ml), the binary formulation was composed of CIP:GAT in the ratio of 1:2. To further enhance the therapeutic efficiency of the quinolone antibiotic powders (that is, to exceed the minimum 1:2 (CIP:GAT) ratio required for *Pseudomonas aeruginosa*), the ratios were adjusted to 1:2.5 (CIP:GAT) for the binary formulation. By using the MIC approach, compatible combinations at suitable proportions can be obtained quickly and is a departure from the tedious trial-and-error screening approach.

All solutions were filtered through a 0.45 μm syringe filter (Millipore of Bedford, Mass., United States of America) prior to spray-drying to minimize blockage due to any undissolved particles at the spray mesh. The spray-dried powders were stored in a desiccator at room temperature for further characterization. The following operating parameters were used for the Nano Spray Dryer:

TABLE 1

Spray drying parameters

| Parameters | |
|---|---|
| Spray mesh size (μm) | 5.5 |
| Feed concentration (w/v %) | 0.75 |
| Nitrogen flow rate (L/min) | 120 |
| Relative spray rate (%) | 4 |
| Inlet Temperature (° C.) | 120 |
| Outlet Temperature (° C.) | 40-45 |
| Yield (%) | 70-80 |

Drug Content Quantification

Drug contents in the spray-dried powders were analyzed via High Performance Liquid Chromatography (HPLC, 1100 series, Agilent Technologies, California, United States of America). For assays of ciprofloxacin hydrochloride and gatifloxacin hydrochloride, a 100 μL aliquot sample was injected into the HPLC system equipped with a Zorbax Extend C-18 column (4.6 mm×150 mm, 3.5 μm) (Agilent Technologies, California, United States of America) as the stationary phase (column temperature 25° C.), and a mixture of 0.025M disodium hydrogen phosphate buffer (adjusted to pH 3.0 with phosphoric acid) and acetonitrile (80:20, v/v) as the mobile phase. A flow rate of 0.5 mL/min and an UV absorbance wavelength of 293 nm were employed for the simultaneous detection of ciprofloxacin hydrochloride and gatifloxacin hydrochloride at retention times of 4.2 and 5.7 minutes respectively.

The composition of the spray-dried particle is shown in Table 2 below. Drug contents (mean±standard deviation, n=3) measured by HPLC.

TABLE 2

Composition of Spray-Dried Particles

| Formulation | Drug Content (w/w %) | | | | % of Ideal (Relative to feed) | |
|---|---|---|---|---|---|---|
| | Feed solution | | Actual (Powder) | | | |
| SD-CIP/GAT | 28.6 | 71.4 | 27.8 ± 0.6 | 72.0 ± 0.7 | 97.2 ± 1.9 | 100.8 ± 1.0 |

Morphology

The morphology of the powder particles was examined by a field emission scanning electron microscopy (FESEM, JEOL JSM-6700). Prior to imaging, the samples were dispersed onto carbon sticky tabs and coated with gold for 80 seconds using a sputter coater (Cressington 208HR, Watford, United Kingdom).

Particle Size Distribution

The particle size distribution was obtained by image analysis of SEM images. To ensure the size distributions were representative of the powder, random samples were taken. Briefly, random sampling of the particles was carried out as follows: particle positioning was determined via the use of a 100-mesh transmission electron microscopy (TEM) grid (GCu100, ProSciTech, Australia) as the reference background (88 segments). A random list of the segments was generated by a random number generator (Minitab Inc., release 13, for Windows). At least 100 particles were measured for each sample from the random fields of view. All the experiments and measurements were performed in triplicate. The particle size distribution is shown in Table 3 below.

TABLE 3

Particle Size of Spray-dried Powder

| | SD-CIP/GAT (μm) |
|---|---|
| $D_{10}$ | 1.24 ± 0.11 |
| $D_{50}$ | 1.91 ± 0.14 |
| $D_{90}$ | 2.96 ± 0.19 |
| Span | 0.91 ± 0.22 |

Figure 2:
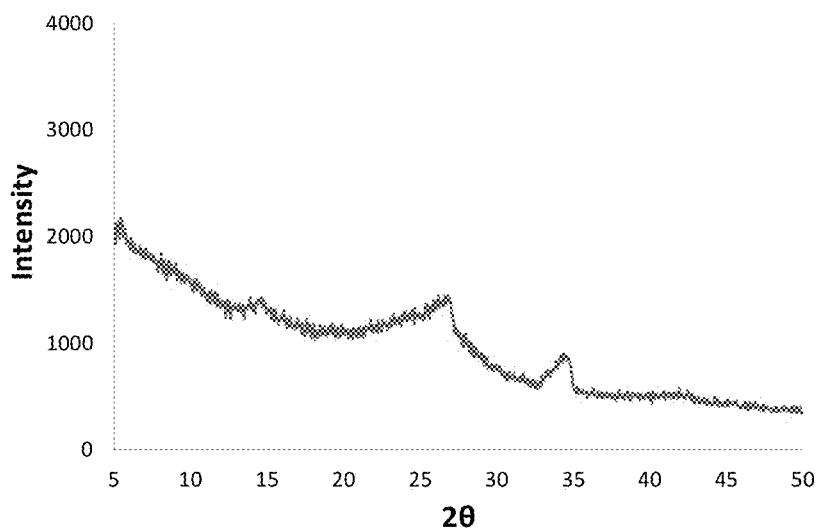
FIG. 2 is a X-ray diffraction pattern of the spray dried SD-CIP/GAT powder.

$D_{10}$—volume diameter under which 10% of the sample resides
$D_{50}$—volume median diameter
$D_{90}$—volume diameter under which 90% of the sample resides
Span = $(D_{90} - D_{10})/D50$ Crystallinity Powder crystallinity of the samples were assessed by powder X-ray diffraction (pXRD) at room temperature using an X-ray diffractometer (D8 Advance; Bruker AXS GmbH, Karlsruhe, Germany). Samples were scanned from 2-50° (2θ) at with an angular increment of 0.04° and at 1 s per step using Cu $K_α$ radiation generated at 35 kV and 40 mA. FIG. 2 shows the XRD pattern of the spray dried particle, indicating that the spray dried particle is amorphous.

In Vitro Aerosol Performance

The aerosol performance was assessed using a Next Generation Impactor (NGI, Copley Scientific, Nottingham, UK) coupled with a United State Pharmacopoeia (USP) stainless steel throat. The method followed the procedure specified for DPIs in the British Pharmacopoeia. Prior to testing, all the eight impactor stages were sprayed with MOLYKOTE® 316 silicone grease release spray (Dow Corning Corp., Midland, Mich.) to minimize particle bounce. Approximately 20±2 mg of spray-dried powder was filled into a hydroxypropyl methylcellulose (HPMC) capsule (size 3, Capsugel®, NJ, USA), loaded into an Aerolizer® inhaler (Novartis Pharmaceuticals, Basel, Switzerland), pierced and then actuated for 4 s at 60 L/min. The powder consisted of respirable-sized particles ($D_{50}$ of 1.91±0.14 μm) capable of achieving a fine particle fraction (FPF) of approximately 40% (ciprofloxacin hydrochloride: 41.3±2.6%; gatofloxacin hydrochloride: 40.9±2.7%).

The flow through the NGI was measured using a calibrated flow meter (TSI Model 4040C, TSI Instrument Ltd., Buckinghanshire, UK), controlled by a high capacity vacuum pump (Model HCP5, Copley Scientific, Nottingham, UK) and a critical flow controller (TPK 2000, Copley Scientific, Nottingham, UK). After actuation, the device, capsule, throat and each part of the NGI were washed separately and thoroughly using deionized water. The solutions were then assayed by HPLC after appropriate sample dilutions were made. Each dispersion test was performed in triplicates to obtain mean values. Temperature and relative humidity (RH) throughout the testing was maintained at 25° C. and 40% respectively.

Figure 3:
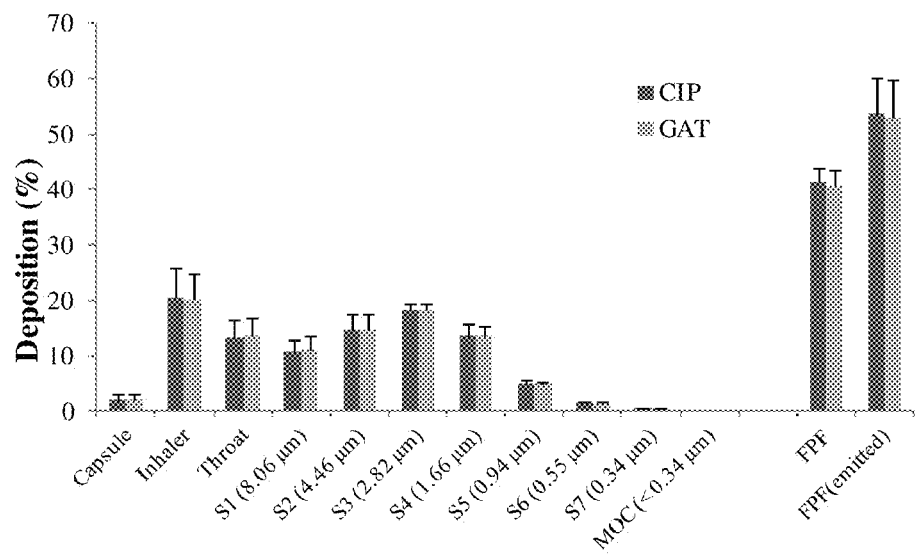
FIG. 3 is a deposition profile of the dry powder formulation when dispersed at 60 L/min.

At a flow rate of 60 L/min, the aerodynamic cut-off diameters of stages 1, 2, 3, 4, 5, 6 and 7 are 8.06, 4.46, 2.82, 1.66, 0.94, 0.55 and 0.34 μm. Particles with diameter size less than 0.34 μm were captured on a Micro Orifice Collector (MOC) beyond stage 7. As can be seen in FIG. 3, a concomitant and uniform in vitro deposition profile could be achieved across all impaction stages when dispersed at 60 L/min.

In this study, fine particle fraction (FPF) represents the mass fraction of drug particles smaller than 5 μm in the aerosol cloud relative to the total mass recovered and was obtained by interpolation to the cumulative percent under-size at 5 μm. FPF (emitted) was obtained when the fine particle dose was expressed relative to the emitted dose.

Example 2

The dry powder formulation as prepared above was then subjected to a time-kill assay against *Pseudomonas aeruginosa* (ATCC 90207). Here, overnight culture of the test *Pseudomonas aeruginosa* was diluted in Mueller-Hinton broth (MHB) to give starting bacterial density of approximately 5×10⁵ CFU/ml. Spray-dried powders were added to the culture such that the final concentrations were at 1×MIC. The culture was then incubated at 37° C. with shaking. Bacterial cell counts were estimated at time 0 and 24 hours. Synergy was defined as a ≥2 $\log_{10}$ decrease in colony count after 24 hours by the combination compared to the most active single agent; indifference as a <2 $\log_{10}$ increase or decrease in colony count at 24 hours by the combination compared with that by the most active single agent and antagonism as a ≥2 $\log_{10}$ increase in colony count after 24 hours by the combination compared with that by the most active single agent.

The results are shown in Table 4 below. As can be seen in Table 4, the spray-dried powder exerted a synergistic effect on the *Pseudomonas aeruginosa*.

TABLE 4

Time kill test results[a]

| Spray dried sample | [b]Remaining count (24 hours) ($\log_{10}$ CFU/ml) | [c]Time-kill assay $\log_{10}$ change | Interaction |
|---|---|---|---|
| SD-CIP | 9.9 | — | — |
| SD-GAT | 6.9 | — | — |
| SD-CIP/GAT | 4.1 | −2.8 | synergy |

[a]Performed in triplicate
[b]after 24 hours incubation with spray-dried powder at 1 × MIC
[c]values represent the $\log_{10}$ change in CFU/ml in the time-kill assay after 24 hours exposure to the most active drug alone
CIP: ciprofloxacin hydrochloride
GAT: gatifloxacin hydrochloride
SD: spray dried Applications The dry powder formulation can be used to treat a bacterial infection. The dry powder formulation can have a synergistic effect on the bacteria and hence may lead to lower dosages of the individual active ingredients, which in turn lead to lower side effects and increased patient compliance.

The dry powder formulation may not require the use of a nebulizer. Due to the dry form of the formulation, clogging of the inhaler during administration of the dry powder formulation may not occur.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:
1. A dry powder formulation comprising a plurality of spray-dried particles, wherein each spray-dried particle is a binary combination consisting of a first pharmaceutically active quinolone and a second pharmaceutically active quinolone at a ratio of at least 1:2.

2. The dry powder formulation of claim 1, wherein said ratio is selected to provide a synergistic effect on a microbial infection.

3. The dry powder formulation of claim 1, wherein said first pharmaceutically active quinolone and said second pharmaceutically active quinolone is independently selected from a fluoroquinolone.

4. The dry powder formulation of claim 3, wherein said fluoroquinolone is selected from the group consisting of ciprofloxacin, gatifloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gemifloxacin, moxifloxacin, sitafloxacin, trovafloxacin, prulifloxacin and pharmaceutically acceptable salts thereof.

5. The dry powder formulation of claim 4, wherein said first pharmaceutically active quinolone is ciprofloxacin and said second pharmaceutically active quinolone is gatifloxacin.

6. The dry powder formulation of claim 5, wherein said first pharmaceutically active quinolone is ciprofloxacin hydrochloride and said second pharmaceutically active quinolone is gatifloxacin hydrochloride.

7. The dry powder formulation of claim 1, wherein said first pharmaceutically active quinolone and said second pharmaceutically active quinolone are present in said formulation in the form of particles having a narrow particle size distribution.

8. The dry powder formulation of claim 7, wherein said particles have a particle size between 500 nm to 4 µm.

9. The dry powder formulation of claim 7, wherein said particles have a mono-modal size distribution with a span $(D_{90}-D_{10})/D_{50}$ of 0.5 to 2.

10. The dry powder formulation of claim 7, wherein said particles have a fine particle fraction in the range of 1% to 99%.

11. The dry powder formulation of claim 1, wherein said dry powder formulation is for administration via a dry powder inhaler.

12. A method for preparing a dry powder formulation comprising the step of co-spray drying a binary system consisting of aqueous solutions of a first pharmaceutically active quinolone and a second pharmaceutically active quinolone to form spray-dried particles of the first pharmaceutically active quinolone and the second pharmaceutically active quinolone, wherein each spray-dried particle is a binary combination consisting of the first pharmaceutically active quinolone and the second pharmaceutically active quinolone at a ratio of at least 1:2.

13. The method of claim 12, wherein said aqueous solutions are provided at a weight ratio of at least 1:2.

14. The method of claim 13, wherein said aqueous solutions are aqueous solutions of ciprofloxacin hydrochloride and gatifloxacin hydrochloride that are provided at a weight ratio of 1:2.5.

15. A dry powder inhaler comprising a dry powder formulation having a plurality of spray-dried particles therein, wherein each spray-dried particle is a binary combination consisting of a first pharmaceutically active quinolone and a second pharmaceutically active quinolone at a ratio of at least 1:2.

16. The dry powder inhaler of claim 15, wherein said dry powder inhaler disperses said dry powder formulation at a rate between 30 to 100 L/min.

17. The dry powder formulation of claim 1 for use in treating a bacterial infection or a respiratory tract infection in a patient.

18. The dry powder formulation of claim 17, wherein said bacterial infection is caused by a bacteria having a genera selected from the group consisting of *Pseudomonas, Escherichia, Haemophilus, Klebsiella, Legionella, Moraxella, Proteus, Acinetobacter, Staphylococcus, Streptococcus, Enterococcus, Mycobacterium, Corynebacterium* and *Mycoplasma*.

19. The dry powder formulation of claim 18, wherein said bacterial infection is caused by a bacteria selected from the group consisting of *Escherichia coli, Haemophilus influenzae, Klebsiella pneumoniae, Legionella pneumophila, Moraxella catarrhalis, Proteus mirabilis, Acinetobacter baumannii, Pseudomonas aeruginosa, Staphyloccus aureus, Streptococcus pneumoniae, Staphylococcus epidermis, Eterococcus faecalis,* and *Streptococcus pyogenes, Mycobacterium tuberculosis,* non-tuberculous mycobacteria, *Corynebacterium diphtheria* and *Mycoplasma pneumoniae*.

20. A method of treating a bacterial infection or respiratory tract infection in a patient, comprising administering the dry powder formulation of claim 1 to the patient, wherein said bacterial infection or respiratory tract infection is selected from the group consisting of pharyngitis, epiglottitis, laryngitis tracheitis, bronchitis, bronchiolitis, pneumonia, and tuberculosis.

* * * * *